US012636310B2

(12) United States Patent
Nagai et al.

(10) Patent No.: US 12,636,310 B2
(45) **Date of Patent: *May 26, 2026**

(54) THERAPEUTIC AGENT FOR SHORT TEAR BREAKUP TIME-TYPE DRY EYE AND EYE DROPS CONTAINING SAME

(71) Applicants: KINKI UNIVERSITY, Higashiosaka (JP); NOF CORPORATION, Tokyo (JP)

(72) Inventors: Noriaki Nagai, Higashiosaka (JP); Ryotaro Seiriki, Higashiosaka (JP); Misa Minami, Higashiosaka (JP); Shunsuke Sakurai, Kawasaki (JP); Eiji Harata, Kawasaki (JP)

(73) Assignees: Kinki University, Osaka (JP); NOF CORPORATION, Tokyo (JP)

( * ) Notice: Subject to any disclaimer, the term of this patent is extended or adjusted under 35 U.S.C. 154(b) by 452 days.

This patent is subject to a terminal disclaimer.

(21) Appl. No.: 18/039,129

(22) PCT Filed: Nov. 24, 2021

(86) PCT No.: PCT/JP2021/042900

§ 371 (c)(1),
(2) Date: May 26, 2023

(87) PCT Pub. No.: WO2022/113970

PCT Pub. Date: Jun. 2, 2022

(65) Prior Publication Data

US 2024/0299443 A1 Sep. 12, 2024

(30) Foreign Application Priority Data

Nov. 30, 2020 (JP) ................................ 2020-197735

(51) Int. Cl.
*A61K 31/80* (2006.01)
*A61K 9/08* (2006.01)
(Continued)

(52) U.S. Cl.
CPC .............. *A61K 31/80* (2013.01); *A61P 27/04* (2018.01)

(58) Field of Classification Search
CPC . A61K 31/80; A61K 9/08; A61P 27/02; A61P 27/04
See application file for complete search history.

(56) References Cited

U.S. PATENT DOCUMENTS 12,102,713 B2 * 10/2024 Nagai .................... A61K 47/32
2015/0024987 A1 1/2015 Matsuoka et al.
(Continued)

FOREIGN PATENT DOCUMENTS

WO 2013/128633 A1 9/2013
WO 2016/140242 A1 9/2016
WO 2017/110874 A1 6/2017

OTHER PUBLICATIONS

Noriaki Nagai, et al., "MPC Polymer Promotes Recovery from Dry Eye via Stabilization of the Ocular Surface", Pharmaceutics, Jan. 27, 2021, pp. 1-17.

(Continued)

*Primary Examiner* — Brenda L Coleman
(74) *Attorney, Agent, or Firm* — Sughrue Mion, PLLC

(57) ABSTRACT

A method of treating short tear breakup time-type dry eye, including a step of administering, to a mammal including a human, (i) a copolymer (P) having three kinds of different constituent units represented by formulae (1a) to (1c) and a weight-average molecular weight of from 5,000 to 2,000,000, wherein a molar ratio among the constituent units [(1a)/(1b)/(1c)] in the copolymer (P) is 100/from 10 to 400/from 2 to 50, or (ii) a composition containing the copolymer (P) at a concentration of from 0.001 w/v % to 1.0 w/v %:

(1a)

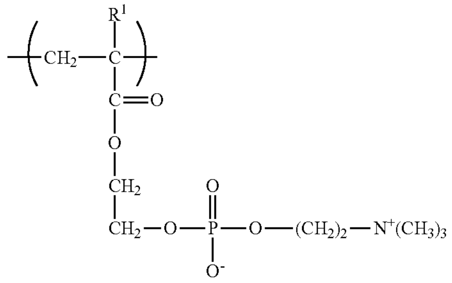

(1b)

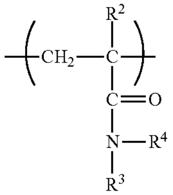

(1c)

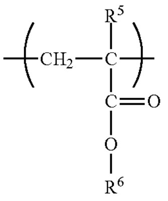

wherein $R^1$ to $R^6$ are as defined herein.

4 Claims, 3 Drawing Sheets

(51) Int. Cl.
*A61P 27/02* (2006.01)
*A61P 27/04* (2006.01)

(56) References Cited

U.S. PATENT DOCUMENTS

| | | | |
|---|---|---|---|
| 2018/0043024 | A1 | 2/2018 | Sakurai et al. |
| 2018/0360872 | A1 | 12/2018 | Sakurai et al. |

OTHER PUBLICATIONS

International Search Report for PCT/JP2021/042900 dated Jan. 25, 2022 [PCT/ISA/210].

* cited by examiner

FIG. 3A
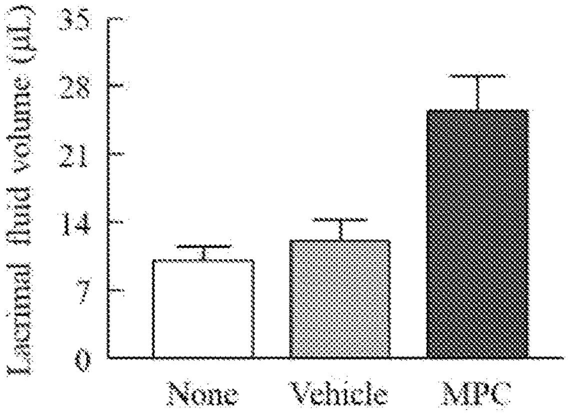
FIG. 3B
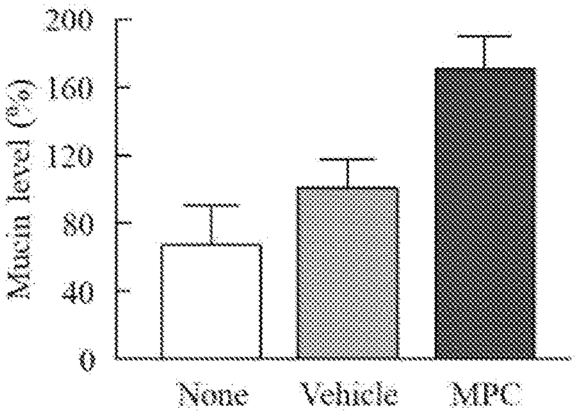
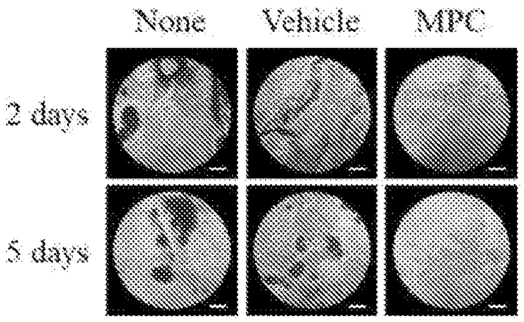
FIG. 3C
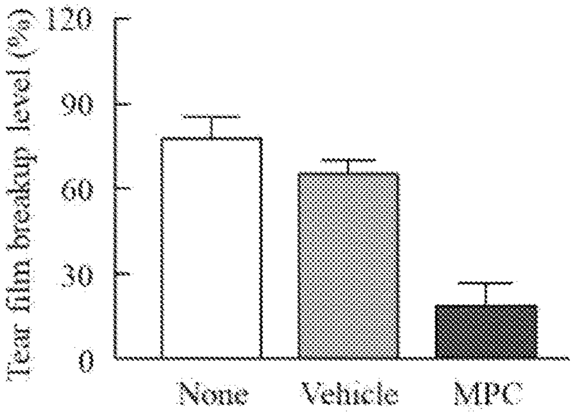
FIG. 3D

THERAPEUTIC AGENT FOR SHORT TEAR BREAKUP TIME-TYPE DRY EYE AND EYE DROPS CONTAINING SAME

CROSS REFERENCE TO RELATED APPLICATIONS

This application is a National Stage of International Application No. PCT/JP2021/042900 filed Nov. 24, 2021, claiming priority based on Japanese Patent Application No. 2020-197735 filed Nov. 30, 2020.

TECHNICAL FIELD

The present invention relates to a therapeutic agent for short tear breakup time (TBUT)-type dry eye containing a copolymer having a specific structure, and an ophthalmic agent containing the therapeutic agent.

The present application claims priority from Japanese Patent Application No. 2020-197735, which is incorporated herein by reference.

BACKGROUND ART

Along with widespread use of smartphones and PCs in recent years, dry eye has spread to a wide range of age groups. Accordingly, it is desired that a dry eye therapeutic drug that is highly efficacious and safe be developed.

The simple term “dry eye” is considered to refer to a wide variety of pathological conditions, and dry eye may be classified into, for example, the following three kinds: (1) aqueous-deficient dry eye, (2) evaporative dry eye, and (3) short tear breakup time-type dry eye (hereinafter sometimes referred to as “short TBUT-type dry eye”).

Optimal treatment methods for those three kinds of dry eye differ from each other. (1) In aqueous-deficient dry eye, a volume of lacrimal fluid to be secreted is reduced in the first place, and hence tear replenishment with artificial tears or a hyaluronic acid ophthalmic solution, or tear reduction-preventing treatment with a punctal plug or the like is often performed (Non Patent Literature 1). (2) In evaporative dry eye, of a mucin layer, an aqueous layer, and a lipid layer that form tears, a lipid layer component is deficient, and hence evaporation of the aqueous layer is enhanced, resulting in dry eye (Non Patent Literature 2). Accordingly, the artificial tears or the hyaluronic acid ophthalmic solution is instilled for the purpose of replenishing evaporated tears, and for example, a warm compress intended to improve the function of Meibomian glands that secrete the lipid layer component, or treatment by lid hygiene is also often used in combination with the instillation. (3) In short tear breakup time-type dry eye, for example, a reduction in function of mucin present on a corneal surface or a reduction in absolute mucin level reduces an ability to spread tears over the corneal surface or retain tears thereon, resulting in dry eye symptoms. Accordingly, an ophthalmic agent for promoting production of mucin present on the corneal surface (Mucosta ophthalmic solution or Diquas ophthalmic solution) is often used (Non Patent Literature 3 and Non Patent Literature 4).

Short tear breakup time-type dry eye is a new type of dry eye found through research in recent years, and hence its treatment method has not necessarily expressed a sufficient effect.

CITATION LIST

Non Patent Literature

[NPL 1] Majid Moshirfar et al., Artificial Tears Potpourri: A Literature Review, Clinical Ophthalmology, 8, 1419-1433, 2014.

[NPL 2] G. N. Foulks, A. J. Bron, Meibomian gland dysfunction: A clinical scheme for description, diagnostics, classification, and grading., Ocul. Surf., 1, 107-126, 2003.

[NPL 3] Gillian M. Keating, Diquafosol Ophthalmic Solution 3%: A Review of Its Use in Dry Eye, Drugs, 75, 911-922, 2015.

[NPL 4] Tomoyuki Kashima et al., Rebamipide Ophthalmic Suspension for the Treatment of Dry Eye Syndrome: A Critical Appraisal, Clinical Ophthalmology, 8, 1003-1010, 2014.

SUMMARY OF INVENTION

Technical Problem

With regard to short tear breakup time-type dry eye, there is currently a demand for a therapeutic agent for short tear breakup time-type dry eye excellent in moisturizing/water-retaining effect on a corneal surface. Accordingly, the present invention provides a therapeutic agent for short TBUT-type dry eye having an excellent dry eye therapeutic effect, and an ophthalmic agent containing the same.

Solution to Problem

The inventors of the present invention have made extensive investigations in order to solve the above-mentioned problem, and as a result, have found that a therapeutic agent for short TBUT-type dry eye containing a copolymer having three kinds of different constituent units at a specific ratio and water achieves sufficient moisturization/water retention on a corneal surface, thereby inducing the promotion of the production of mucin on the corneal surface and being efficacious for dry eye treatment. Thus, the inventors have completed the present invention.

That is, a therapeutic agent for short TBUT-type dry eye, and an ophthalmic agent containing the same, of the present invention are as described below.

1. A therapeutic agent for short tear breakup time-type dry eye, including a copolymer (P) which has constituent units represented by the following general formulae (1a) to (1c), and has a weight-average molecular weight of from 5,000 to 2,000,000, wherein a concentration of the copolymer (P) is from 0.001 w/v % to 1.0 w/v %, and wherein a molar ratio among the constituent units [(1a)/(1b)/(1c)] in the copolymer (P) is 100/from 10 to 400/from 2 to 50:

(1a)

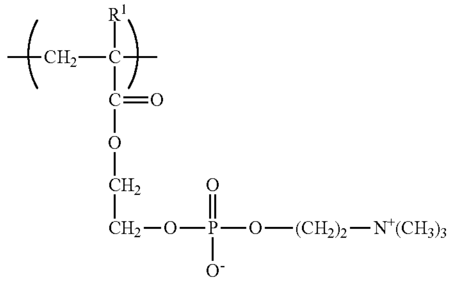

in the general formula (1a), $R^1$ represents a hydrogen atom or a methyl group;

(1b)

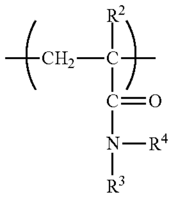

in the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other; and (1c)

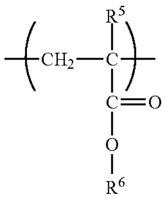

in the general formula (1c), $R^5$ represents a hydrogen atom or a methyl group, and $R^6$ represents a hydrocarbon group having 12 to 24 carbon atoms.

2. The therapeutic agent for short tear breakup time-type dry eye according to the above-mentioned item 1, wherein the copolymer (P) consists of the constituent unit represented by the general formula (1a), the constituent unit represented by the general formula (1b), and the constituent unit represented by the general formula (1c).

3. The therapeutic agent for short tear breakup time-type dry eye according to the above-mentioned item 1 or 2, wherein the constituent unit represented by the general formula (1b) is N,N-dimethylacrylamide, and the constituent unit represented by the general formula (1c) is stearyl methacrylate.

4. An ophthalmic agent, including the therapeutic agent for short tear breakup time-type dry eye of any one of the above-mentioned items 1 to 3.

5. A method of treating short tear breakup time-type dry eye, including the following step:

a step of administering, to a mammal including a human, a copolymer (P) which has constituent units represented by the following general formulae (1a) to (1c), has a weight-average molecular weight of from 5,000 to 2,000,000, and has a molar ratio among the constituent units [(1a)/(1b)/(1c)] of 100/from 10 to 400/from 2 to 50, or a composition containing the copolymer (P) at a concentration of from 0.001 w/v % to 1.0 w/v %:

(1a)

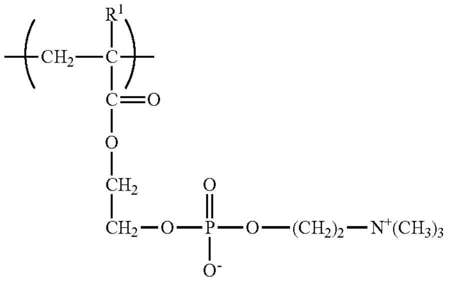

in the general formula (1a), $R^1$ represents a hydrogen atom or a methyl group;

(1b)

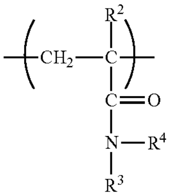

in the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other; and (1c)

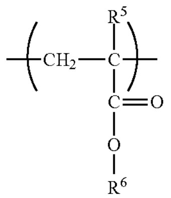

in the general formula (1c), $R^5$ represents a hydrogen atom or a methyl group, and $R^6$ represents a hydrocarbon group having 12 to 24 carbon atoms.

6. The method of treating short tear breakup time-type dry eye according to the above-mentioned item 5, wherein the copolymer (P) consists of the constituent unit represented by the general formula (1a), the constituent unit represented by the general formula (1b), and the constituent unit represented by the general formula (1c).

7. The method of treating short tear breakup time-type dry eye according to the above-mentioned item 6 or 7, wherein the constituent unit represented by the general formula (1b) is N,N-dimethylacrylamide, and the constituent unit represented by the general formula (1c) is stearyl methacrylate.

8. A use of a copolymer (P) or a composition for production of a therapeutic agent for short tear breakup time-type dry eye, the copolymer (P) having constituent units represented by the following general formulae (1a) to (1c), having a weight-average molecular weight of from 5,000 to 2,000,000, and having a molar ratio among the constituent units [(1a)/(1b)/(1c)] of 100/from 10 to 400/from 2 to 50, the composition containing the copolymer (P) at a concentration of from 0.001 w/v % to 1.0 w/v %:

(1a)

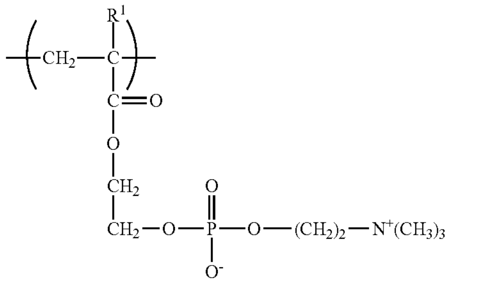

in the general formula (1a), $R^1$ represents a hydrogen atom or a methyl group;

(1b)

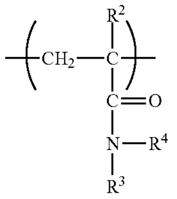

in the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other; and (1c)

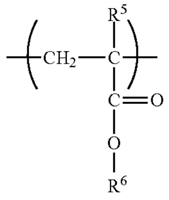

in the general formula (1c), $R^5$ represents a hydrogen atom or a methyl group, and $R^6$ represents a hydrocarbon group having 12 to 24 carbon atoms.

9. The use for production of a therapeutic agent for short tear breakup time-type dry eye according to the above-mentioned item 8, wherein the copolymer (P) consists of the constituent unit represented by the general formula (1a), the constituent unit represented by the general formula (1b), and the constituent unit represented by the general formula (1c).

10. The use for production of a therapeutic agent for short tear breakup time-type dry eye according to the above-mentioned item 8 or 9, wherein the constituent unit represented by the general formula (1b) is N,N-dimethylacrylamide, and the constituent unit represented by the general formula (1c) is stearyl methacrylate.

Advantageous Effects of Invention

It has been recognized that the therapeutic agent for short TBUT-type dry eye of the present invention can achieve sufficient moisturization/water retention on a corneal surface, and induce the promotion of the production of mucin on the corneal surface. Further, the ophthalmic agent containing the therapeutic agent for short TBUT-type dry eye of the present invention can provide an ophthalmic agent having an excellent therapeutic effect on short TBUT-type dry eye.

BRIEF DESCRIPTION OF DRAWINGS

FIG. 2A shows the results of observation of the external appearances of removed rabbit corneas, and FIG. 2B shows temporal changes in weight of removed rabbit corneas. In the figures, "Vehicle" represents a saline instillation group of normal rabbits that have not developed dry eye and "MPC" represents a MPC polymer (solution containing 0.1 w/v % of the copolymer (P)) instillation group of normal rabbits that have not developed dry eye.

FIGS. 3A to 3D show the influences of treatment with the copolymer (P) on the lacrimal fluid volume FIG. 3A, mucin level FIG. 3B, and tear film breakup (FIG. 3C and FIG. 3D) of a dry eye rabbit model. In the figures, "None" represents a non-instillation group of rabbits that have developed dry eye, "Vehicle" represents a saline instillation group of rabbits that have developed dry eye, and "MPC" represents a MPC polymer (solution containing 0.1 w/v % of the copolymer (P)) instillation group of rabbits that have developed dry eye. Scale bars each represent a size of 1 mm. FIG. 3C shows photographs of rabbit corneas taken in a magnified manner. Black portions in the photographs are dry eye spots, and indicate portions where tear film breakup/breakage has occurred. For the dry eye model, an experiment was performed with 9 eyes (n=9), instillation was performed once a day (two p.m.), and tears were collected with Schirmer test paper at six p.m. after 5 days from the start of the experiment.

DESCRIPTION OF EMBODIMENTS

Figure 1A:
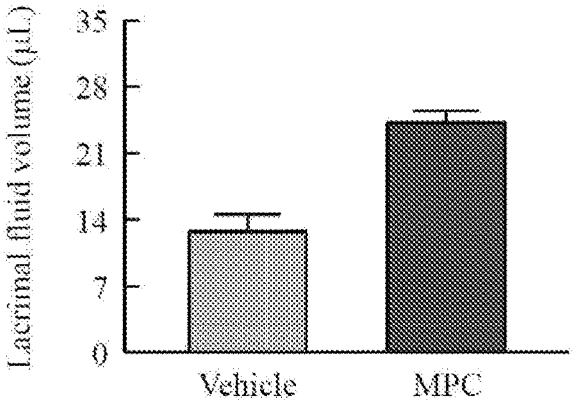
FIG. 1A and FIG. 1B show the influences of instillation of a copolymer (P) on the lacrimal fluid volume (FIG. 1A) and TBUT (FIG. 1B) of normal rabbits. In the figures, "Normal" represents a non-instillation group of normal rabbits that have not developed dry eye, "Vehicle" represents a saline instillation group of normal rabbits that have not developed dry eye, and "MPC" represents a MPC polymer (solution containing 0.1 w/v % of the copolymer (P) instillation group of normal rabbits that have not developed dry eye. For the normal rabbits, an experiment was performed with 8 eyes (n=8), and tears were collected 2 hours after instillation.

The present invention is described in more detail below.

A therapeutic agent for short TBUT-type dry eye of the present invention contains a copolymer (P) which has constituent units represented by the following general formulae (1a) to (1c), and has a weight-average molecular weight of from 5,000 to 2,000,000, and water. Further, a concentration of the copolymer (P) is from 0.001 w/v % to 1.0 w/v %. In addition, a molar ratio among the constituent units [(1a)/(1b)/(1c)] in the copolymer (P) is 100/from 10 to 400/from 2 to 50.

(1a)

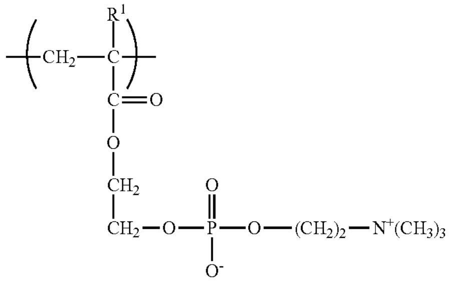

In the general formula (1a), $R^1$ represents a hydrogen atom or a methyl group.

(1b)

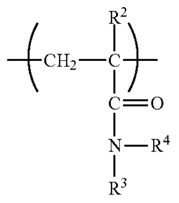

In the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other.

(1c)

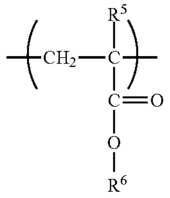

In the general formula (1c), $R^5$ represents a hydrogen atom or a methyl group, and $R^6$ represents a hydrocarbon group having 12 to 24 carbon atoms.

The configuration of the present invention is described below.

As used herein, the term "(meth)acrylate" means "acrylate or methacrylate", and the same applies to other similar terms. In addition, herein, when preferred numerical ranges (e.g., the ranges of a concentration or a weight-average molecular weight) are described in stages, the respective lower limit values and upper limit values may be independently combined with each other. For example, in the description: "preferably 10 or more, more preferably 20 or more, and preferably 100 or less, more preferably 90 or less", the "preferred lower limit value: 10" and the "more preferred upper limit value: 90" may be combined to obtain a range of "10 or more and 90 or less". In addition, for example, also in the description: "preferably from 10 to 100, more preferably from 20 to 90", a range of "from 10 to 90" may be similarly obtained.

<Copolymer (P)>

The copolymer (P) to be used (contained) in the therapeutic agent for short TBUT-type dry eye of the present invention is a copolymer which has the constituent units represented by the general formulae (1a) to (1c), and has a weight-average molecular weight of from 5,000 to 2,000,000.

[Constituent Unit Represented by General Formula (1a)]

The copolymer (P) to be used in the present invention has the constituent unit represented by the following general formula (1a), that is, a constituent unit having a phosphorylcholine structure (hereinafter sometimes referred to as "PC constituent unit"). By virtue of the copolymer (P) having the PC constituent unit, hydrophilicity can be imparted to the copolymer (P), to thereby express an excellent moisturizing action/water-retaining effect on a corneal surface.

(1a)

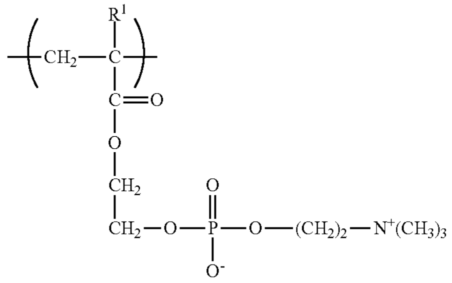

In the general formula (1a), $R^1$ represents a hydrogen atom or a methyl group.

The PC constituent unit may be obtained by copolymerizing a monomer represented by the following general formula (1a') (hereinafter sometimes referred to as "PC monomer"). From the viewpoint of availability, the PC monomer is preferably 2-((meth)acryloyloxy)ethyl 2-(trimethylammonio)ethyl phosphate, more preferably 2-(methacryloyloxy)ethyl 2-(trimethylammonio)ethyl phosphate represented by the following formula (1a') (hereinafter sometimes referred to as "2-methacryloyloxyethyl phosphorylcholine").

(1a')

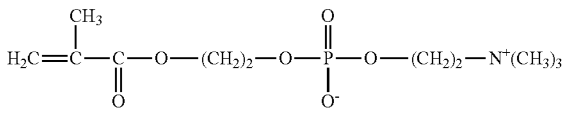

From the viewpoint of expressing an excellent moisturizing action/water-retaining action on a corneal surface, the content of the PC constituent unit in the copolymer (P) is preferably 10 mol % or more, more preferably 20 mol % or more, still more preferably 25 mol % or more, and is preferably 80 mol % or less, more preferably 75 mol % or less, still more preferably 70 mol % or less.

[Constituent Unit Represented by General Formula (1b)]

The copolymer (P) to be used in the present invention has the constituent unit represented by the following general formula (1b) (hereinafter sometimes referred to as "amide constituent unit"). By virtue of increasing the molecular weight of the copolymer (P) with the amide constituent unit, the retainability of the copolymer (P) on a corneal surface can be improved.

(1b)

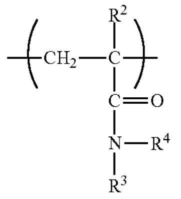

In the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other.

The amide constituent unit may be obtained by copolymerizing (meth)acrylamide or a (meth)acrylamide derivative that is a monomer represented by the following general formula (1b') (hereinafter sometimes referred to as "amide monomer").

(1b')

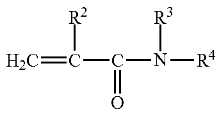

$R^2$, $R^3$, and $R^4$ in the general formula (1b') each have the same meaning as that in the general formula (1b).

Specific examples of the monomer represented by the formula (1b') include N,N-dimethyl (meth)acrylamide, N,N-diethyl (meth)acrylamide, and N-acryloylmorpholine.

In the copolymer (P), when the number of the PC constituent units is set to 100, the ratio [(1a)/(1b)] of the number of the PC constituent units (1a) to the number of the amide constituent units (1b) is 100/from 10 to 400, preferably 100/from 30 to 250, more preferably 100/from 50 to 150, still more preferably 100/from 70 to 120, yet still more preferably 100/from 80 to 110, yet still more preferably 100/from 80 to 100. When the ratio of the number of the amide constituent units to the number of the PC constituent units is excessively large, there is a risk in that aseptic filtration to be performed in the production of the solution of the present invention may become difficult. Meanwhile, when the ratio is excessively small, the increase in molecular weight of the copolymer (P) becomes insufficient, resulting in a risk in that the retaining effect of the copolymer (P) on a corneal surface may become insufficient.

[Constituent Unit Represented by General Formula (1c)]

The copolymer (P) to be used in the present invention has the constituent unit represented by the following general formula (1c) (hereinafter sometimes referred to as "hydrophobic constituent unit"). By virtue of the copolymer (P) having the hydrophobic constituent unit, the adhesiveness of the copolymer (P) to a corneal surface can be improved, and besides, its ability to form a physically crosslinked gel through a hydrophobic interaction can be enhanced to further enhance the water-retaining action/moisturizing effect of the copolymer (P).

(1c)

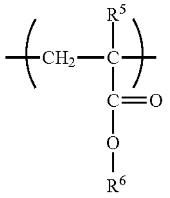

In the general formula (1c), $R^5$ represents a hydrogen atom or a methyl group, and $R^6$ represents a hydrocarbon group having 12 to 24 carbon atoms.

$R^6$ in the general formula (1c) represents a hydrocarbon group having 12 to 24 carbon atoms, and the hydrocarbon group may be linear or branched, but is preferably linear. Examples of the hydrocarbon group having 12 to 24 carbon atoms include a lauryl group, a myristyl group, a cetyl group, a stearyl group, an oleyl group, and a behenyl group.

From the viewpoint of improving the adhesiveness of the copolymer (P) to a corneal surface, $R^6$ represents preferably a hydrocarbon group having 12 to 20 carbon atoms, more preferably a hydrocarbon group having 12 to 18 carbon atoms out of those groups, and specifically, preferably represents a lauryl group or a stearyl group.

The hydrophobic constituent unit may be obtained by copolymerizing a monomer represented by the following formula (1c') (hereinafter sometimes referred to as "hydrophobic monomer").

(1c')

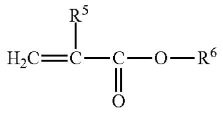

$R^5$ and $R^6$ in the general formula (1c') each have the same meaning as that in the general formula (1c).

Specific examples of the hydrophobic monomer represented by the general formula (1c') include linear alkyl (meth)acrylates, such as lauryl (meth)acrylate, myristyl (meth)acrylate, cetyl (meth)acrylate, stearyl (meth)acrylate, oleyl (meth)acrylate, and behenyl (meth)acrylate.

From the viewpoint of improving the adhesiveness of the copolymer (P) to a corneal surface, the hydrophobic monomer represented by the general formula (1c') is preferably lauryl (meth)acrylate, myristyl (meth)acrylate, or stearyl (meth)acrylate, more preferably lauryl methacrylate or stearyl methacrylate, still more preferably stearyl methacrylate out of those groups.

In the copolymer (P), when the number of the PC constituent units is set to 100, the ratio [(1a)/(1c)] of the number of the PC constituent units (1a) to the number of the hydrophobic constituent units (1c) is 100/from 2 to 50, preferably 100/from 5 to 25, more preferably 100/from 7 to 20, still more preferably 100/from 8 to 15. When the ratio of the number of the hydrophobic constituent units to the number of the PC constituent units is excessively small, there is a risk in that the adhesiveness of the copolymer (P) to a corneal surface may become insufficient. Meanwhile, when the ratio is excessively large, the hydrophilicity of the copolymer (P) is reduced, and hence its solubility in an aqueous solution is reduced, resulting in a risk in that it may become difficult to produce the therapeutic agent for short TBUT-type dry eye.

In light of the foregoing, from viewpoints regarding the moisturizing action/water-retaining action of the copolymer (P) and the adhesiveness thereof to a corneal surface, the molar ratio among the constituent units [(1a)/(1b)/(1c)] in the copolymer (P) is 100/from 10 to 400/from 2 to 50, preferably 100/from 30 to 250/from 5 to 25, more preferably 100/from 50 to 150/from 5 to 25, still more preferably 100/from 70 to 120/from 5 to 25, yet still more preferably 100/from 80 to 110/from 7 to 20, yet still more preferably 100/from 80 to 100/from 8 to 15.

The copolymer (P) to be used in the present invention only needs to have at least one kind of each of the PC constituent unit, the amide constituent unit, and the hydrophobic constituent unit, and for example, may contain a plurality of kinds of PC constituent units.

[Weight-Average Molecular Weight of Copolymer (P)]

The weight-average molecular weight of the copolymer (P) is from 5,000 to 2,000,000, preferably 10,000 or more, more preferably 20,000 or more, still more preferably 50,000 or more, yet still more preferably 700,000 or more, and is preferably 1,800,000 or less, more preferably 1,600,000 or less, still more preferably 1,500,000 or less, yet still more preferably 1,300,000 or less, yet still more preferably 1,100,000 or less.

When the weight-average molecular weight is less than 5,000, there is a risk in that the adhesiveness of the copolymer (P) to a corneal surface may become insufficient, and there is a risk in that a therapeutic effect on short TBUT-type dry eye cannot be expected. When the weight-average molecular weight is more than 2,000,000, there is a risk in that the viscosity of the therapeutic agent for short TBUT-type dry eye may be increased to make its handling difficult.

The weight-average molecular weight of the copolymer (P) refers to a value according to gel permeation chromatography (GPC) measurement. Specifically, the weight-average molecular weight of the copolymer (P) refers to a molecular weight in terms of polyethylene glycol measured using as an eluent any one of chloroform, dimethylformamide, tetrahydrofuran, methanol, and liquids obtained by combining these solvents.

[Method of Producing Copolymer (P)]

The copolymer (P) may be prepared by, for example, copolymerizing the above-mentioned monomers in accordance with a method described in WO 2013/128633 A1. In addition, the copolymer (P) is generally a random copolymer, but may be an alternate copolymer or block copolymer in which the constituent units are regularly arranged, and may have a graft structure as a part thereof.

[Concentration of Copolymer (P)]

In the therapeutic agent for short TBUT-type dry eye of the present invention, the concentration of the copolymer (P) is 0.001 w/v % or more, preferably 0.002 w/v % or more, more preferably 0.003 w/v % or more, still more preferably 0.005 w/v % or more, and is 1.0 w/v % or less, preferably 0.8 w/v % or less, more preferably 0.6 w/v % or less, still more preferably 0.5 w/v % or less. When the concentration of the copolymer (P) is less than 0.001 w/v %, a sufficient therapeutic effect on short TBUT-type dry eye is not obtained. A concentration of more than 1.0 w/v % is economically disadvantageous because an effect commensurate with the blending amount is not obtained.

In the present invention, "w/v %" is an expression of the mass of a given component in 100 ml of a solution in grams (g). For example, the description that "a solution of the present invention contains 1.0 w/v % of the copolymer (P)" means that 100 ml of the solution contains 1.0 g of the copolymer (P).

[Solvent]

The therapeutic agent for short TBUT-type dry eye of the present invention may use water as a solvent.

Water to be generally used in the production of a pharmaceutical or a medical device may be used as the water to be used for the therapeutic agent for short TBUT-type dry eye of the present invention. Specifically, for example, ion-exchanged water, purified water, sterile purified water, distilled water, and water for injection may be used.

[Other Components]

The therapeutic agent for short TBUT-type dry eye of the present invention may further contain the following additives as required in addition to the copolymer (P).

Examples of the additives may include additives that have been used for related-art ophthalmic agents and the like, and examples thereof include a vitamin, an amino acid, a sugar, a cooling agent, an inorganic salt, an organic acid salt, an acid, a base, an antioxidant, a stabilizing agent, and an antiseptic agent.

Examples of the vitamin include flavin adenine dinucleotide sodium, cyanocobalamin, retinol acetate, retinol palmitate, pyridoxine hydrochloride, panthenol, sodium pantothenate, and calcium pantothenate.

Examples of the amino acid include aspartic acid and salts thereof and aminoethylsulfonic acid.

Examples of the sugar include glucose, mannitol, sorbitol, xylitol, and trehalose.

Examples of the cooling agent include menthol and camphor.

Examples of the inorganic salt include sodium chloride and potassium chloride.

An example of the organic acid salt is sodium citrate.

Examples of the acid include phosphoric acid, citric acid, sulfuric acid, and acetic acid.

Examples of the base include trishydroxymethylaminomethane and monoethanolamine.

Examples of the antioxidant include tocopherol acetate and dibutylhydroxytoluene.

Examples of the stabilizing agent include sodium edetate and glycine.

Examples of the antiseptic agent include benzalkonium chloride, chlorhexidine gluconate, potassium sorbate, and polyhexanide hydrochloride.

[Method of Producing Ophthalmic Agent Solution]

An ophthalmic agent containing the therapeutic agent for short TBUT-type dry eye of the present invention may be produced by a general method of producing an ophthalmic agent, involving mixing and stirring the copolymer (P), water, and as required, other components. The resultant ophthalmic agent may be subjected to an operation such as aseptic filtration as required.

[Method of Treating Short Tear Breakup Time-Type Dry Eye]

The present invention also encompasses a method of treating short tear breakup time-type dry eye, including the following step:

a step of administering, to a mammal including a human, a copolymer (P) which has constituent units represented by the following general formulae (1a) to (1c), has a weight-average molecular weight of from 5,000 to 2,000,000, and has a molar ratio among the constituent units [(1a)/(1b)/(1c)] of 100/from 10 to 400/from 2 to 50, or a composition containing the copolymer (P) at a concentration of from 0.001 w/v % to 1.0 w/v %:

(1a)

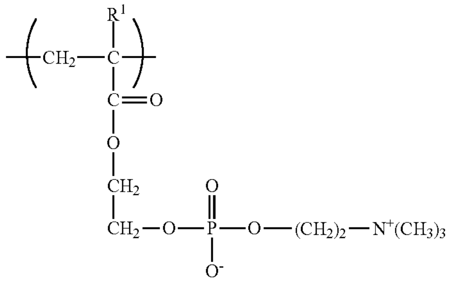

in the general formula (1a), $R^1$ represents a hydrogen atom or a methyl group;

(1b)

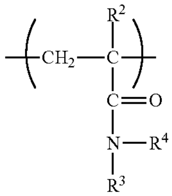

in the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other; and (1c)

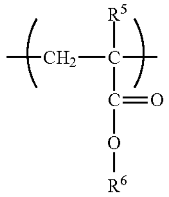

in the general formula (1c), $R^5$ represents a hydrogen atom or a methyl group, and $R^6$ represents a hydrocarbon group having 12 to 24 carbon atoms.

The method of treating short tear breakup time-type dry eye of the present invention is not particularly limited, but for example, 0.01 mL to 0.2 mL of the therapeutic agent for short tear breakup time-type dry eye of the present invention may be dropped onto an eye (eyeball) from any angle, from 1 to 10 times, from 1 to 8 times, from 1 to 6 times, from 1 to 4 times, or from 1 to 3 times (preferably in the morning, the afternoon, and the evening) a day.

A target to be treated, which is not particularly limited, is a mammal including a human, and the target is preferably a patient in need of prevention, alleviation, amelioration, or treatment of short tear breakup time-type dry eye.

[Use of Copolymer (P) for Production of Therapeutic Agent for Short Tear Breakup Time-Type Dry Eye]

The present invention also encompasses a use of a copolymer (P) for production of a therapeutic agent for short tear breakup time-type dry eye.

A use of a copolymer (P) or a composition for production of a therapeutic agent for short tear breakup time-type dry eye, the copolymer (P) having constituent units represented by the following general formulae (1a) to (1c), having a weight-average molecular weight of from 5,000 to 2,000,000, and having a molar ratio among the constituent units [(1a)/(1b)/(1c)] of 100/from 10 to 400/from 2 to 50, the composition containing the copolymer (P) at a concentration of from 0.001 w/v % to 1.0 w/v %:

(1a)

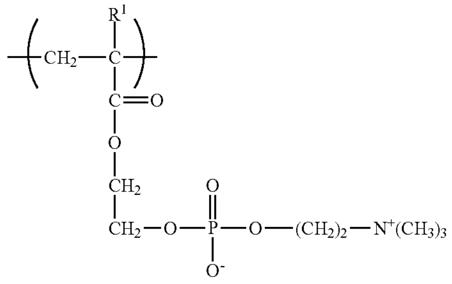

in the general formula (1a), $R^1$ represents a hydrogen atom or a methyl group;

(1b)

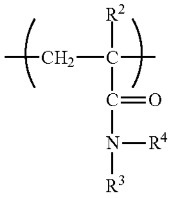

in the general formula (1b), $R^2$ represents a hydrogen atom or a methyl group, and $R^3$ and $R^4$ each independently represent a hydrogen atom, a methyl group, or an ethyl group, or represent a morpholino group by being bonded to each other; and (1c)

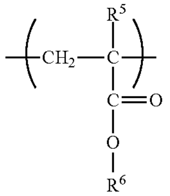

in the general formula (1c), $R^5$ represents a hydrogen atom or a methyl group, and $R^6$ represents a hydrocarbon group having 12 to 24 carbon atoms.

The copolymer (P) to be used in the therapeutic agent for short tear breakup time-type dry eye or the method of treating short tear breakup time-type dry eye of the present invention may be exemplified by the following.

1) The constituent unit represented by (1a) is 2-(methacryloyloxy)ethyl 2-(trimethylammonio)ethyl phosphate, the constituent unit represented by (1b) is N,N-dimethylacrylamide, and the constituent unit represented by (1c) is stearyl methacrylate.
2) The constituent unit represented by (1a) is 2-(methacryloyloxy)ethyl 2-(trimethylammonio)ethyl phosphate, the constituent unit represented by (1b) is N,N- dimethylacrylamide, and the constituent unit represented by (1c) is lauryl methacrylate.

3) The constituent unit represented by (1a) is 2-(methacryloyloxy)ethyl 2-(trimethylammonio)ethyl phosphate, the constituent unit represented by (1b) is N,N-dimethylacrylamide, and the constituent unit represented by (1c) is myristyl methacrylate.

Examples

The present invention is hereinafter described in more detail by way of Example and Comparative Example. However, the present invention is by no means limited thereto.

[Copolymer (P)]

A copolymer (1) described below was used as the copolymer (P). The copolymer (1) was prepared by a method described in Examples of WO 2013/128633 A1.

[Copolymer (1)]

A copolymer using 2-(methacryloyloxy)ethyl 2-(trimethylammonio)ethyl phosphate (2-methacryloyloxyethyl phosphorylcholine) represented by the general formula (1a') as a PC monomer, N,N-dimethylacrylamide as an amide monomer, and stearyl methacrylate as a hydrophobic monomer.

Molar ratio among constituent units $$[(1a)/(1b)/(1c)] = 100/90/10$$

Weight-average molecular weight: 1,000,000

In this Example, the weight-average molecular weight of the copolymer (P) was measured under the following analysis conditions using a sample solution obtained by dissolving 5 mg of each obtained copolymer in a methanol/chloroform mixed liquid (80/20).

Column: PLgel-mixed-C

Standard substance: polyethylene glycol

Detector: differential refractometer RI-8020 (manufactured by Tosoh Corporation)

Calculation method for weight-average molecular weight: molecular weight calculation program (GCP program for SC-8020)

Flow rate: 1 mL per minute

Injection volume: 100 μL

Column oven: constant temperature around 40° C.

[Measurement Test of Therapeutic Effect on Short Tear Breakup Time-Type Dry Eye]

In accordance with the following procedures (reference: Pharmaceutics 2020, 12, 155), various kinds of measurement were performed in order to determine a therapeutic effect on short tear breakup time-type dry eye.

[Tear Breakup Time Measurement]

(1) N-Acetylcysteine was dissolved in saline (sodium chloride: 0.9%, water: balance) to prepare a 10 w/v % solution.

(2) The solution prepared in (1) was used and administered by instillation to a male Japanese white rabbit 6 times in total at a single dose of 50 μL and at intervals of 2 hours.

(3) The day after the instillation administration, the dry eye state of the male Japanese white rabbit was recognized, and then the rabbit was used as a dry eye model that had developed short tear breakup time-type dry eye.

(4) The dry eye model was measured for its dry eye state (measured for its TBUT) through observation with a dry eye measurement apparatus (DR-1α, Kowa Company, Ltd.).

(5) 50 μL of a solution of Example or Comparative Example described below was administered by instillation once a day for 2 days.

(6) After that, the dry eye state was measured again by the procedure shown in (4) (2 days).

(7) 50 μL of the solution of Example or Comparative Example was administered by instillation once a day for 3 days.

(8) After that, the dry eye state was measured again by the procedure shown in (4) (5 days).

[Measurement of Lacrimal Fluid Volume]

A lacrimal fluid volume was measured using Schirmer test paper.

[Mucin Level Measurement Test]

A mucin level measurement test was performed in accordance with the following procedure.

(1) N-Acetylcysteine was dissolved in saline (sodium chloride: 0.9%, water: balance) to prepare a 10 w/v % solution.

(2) Tears were collected with Schirmer test paper for 5 minutes, and a mucin level in the tears was measured using a tear mucin assay kit (manufactured by Cosmo Bio) and adopted as an initial value.

(3) The solution prepared in (1) was used and administered by instillation to a male Japanese white rabbit 6 times in total at a single dose of 50 μL and at intervals of 2 hours.

(4) The day after the instillation administration, the dry eye state of the male Japanese white rabbit was recognized, and then the rabbit was used as a dry eye model that had developed short tear breakup time-type dry eye.

(5) The dry eye model or a normal rabbit was measured for its mucin level by the procedure shown in (2).

(6) 50 μL of the solution of Example or Comparative Example was administered by instillation once a day for a total of 5 days.

(7) After that, the mucin level was measured again by the procedure shown in (2).

The initial value and the mucin level after 5 days were compared, and were converted into percentages to calculate mucin levels (%).

[Calculation of Tear Film Breakup Level]

At the time point when the dry eye model (rabbit) was generated, its TBUT was measured, and then an image thereof was acquired. The acquired image was captured with image processing software Image J, and an area in which a tear was broken up was calculated (initial value). The dry eye model was repeatedly subjected to vehicle instillation, MPC instillation, or no instillation for 5 days. After 5 days, the TBUT was measured again, and then an image was acquired. The acquired image was captured with Image J, and an area in which a tear was broken up was calculated (after 5 days).

The area in which a tear was broken up on the first day and the area in which a tear was broken up after 5 days were compared, and were converted into percentages to calculate tear film breakup levels (%).

[Corneal Surface Moisture Retention Time Measurement Test]

A cornea removed from the rabbit used in the tear breakup time measurement was immersed in the solution of Example described below or saline of Comparative Example (sodium chloride: 0.9%, water: balance). After having been taken out, the cornea was left at rest for 150 minutes, during which its weight was measured at a plurality of time points to investigate temporal changes in weight. In addition, images of external appearances immediately after being taken out (after 0 minutes) and after 60 minutes were acquired with a digital camera.

Example

An aqueous solution containing 1 w/v % of the copolymer (P) was prepared in advance, and 0.1 mL thereof and saline (sodium chloride: 0.9%, water: balance) were used to prepare a solution containing 0.1 w/v % of the copolymer (P), which was used as the solution of Example. Saline (sodium chloride: 0.9%, water: balance) was used as the solution of Comparative Example.

[Evaluation of Instillation Treatment of Normal Rabbits (that have not Developed Dry Eye)]

Figure 1B:
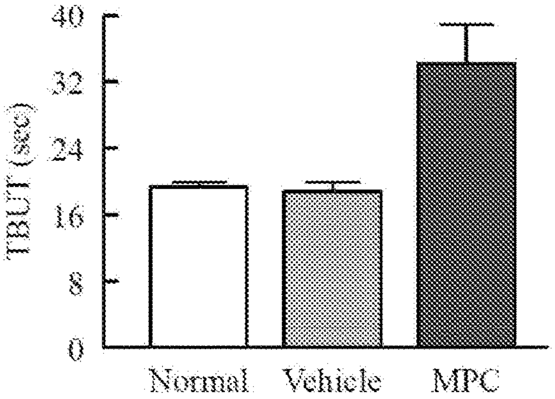

Normal rabbits were subjected to instillation treatment with the solution of Example (in FIGS. 1A and 1B: "MPC") or saline (sodium chloride: 0.9%, water: balance, "Vehicle (Comparative Example)" in FIGS. 1A and 1B), and their lacrimal fluid volumes and TBUTs were measured. As Reference Example, the TBUT of a non-instillation group of normal rabbits that have not developed dry eye was measured. The results are shown in FIGS. 1A and 1B.

[Evaluation of Instillation Treatment of Short Tear Breakup Time-type Dry Eye Rabbit Model]

The dry eye rabbit model was subjected to instillation treatment with the solution of Example (in FIGS. 3A to 3D: "MPC") or saline (sodium chloride: 0.9%, water: balance, "Vehicle (Comparative Example)" in FIGS. 3A to 3D), and its lacrimal fluid volume, mucin level, and tear film breakup were measured. As Reference Example, the lacrimal fluid volume, mucin level, and tear film breakup of a non-instillation group of rabbits that had developed dry eye were measured. The results are shown in FIGS. 3A to 3D.

[Evaluation of Instillation Treatment of Removed Rabbit Cornea]

Figure 2A:
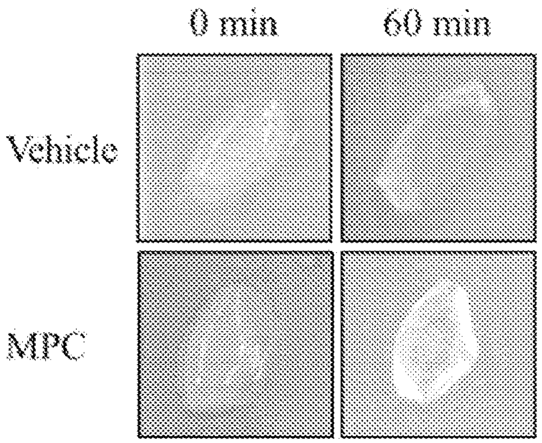
FIG. 2A and FIG. 2B show the influences of treatment with the copolymer (P) on the moisture retention time of removed rabbit corneas.
Figure 2B:
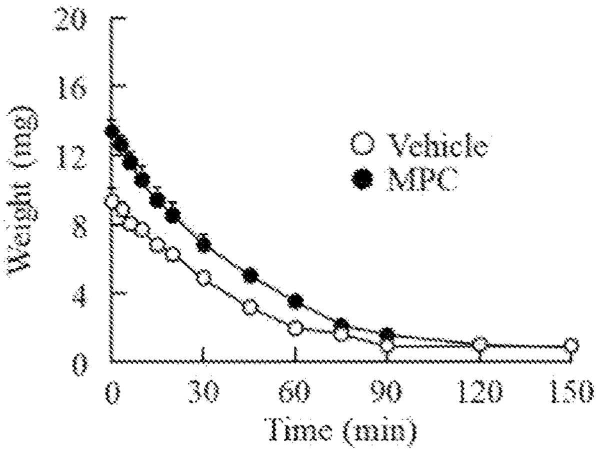

A rabbit cornea removed from each of the normal rabbits after the above-mentioned evaluation was subjected to instillation treatment with the solution of Example (in FIGS. 2A and 2B: "MPC") or saline (sodium chloride: 0.9%, water: balance, "Vehicle (Comparative Example)" in FIGS. 2A and 2B), and the moisture retention time of the cornea was measured. The results are shown in FIGS. 2A and 2B.

<Results>

With regard to the results of the evaluation of the instillation treatment of normal rabbits, when the normal rabbits were subjected to the instillation treatment, an increase in lacrimal fluid volume (FIG. 1A) and an increase in TBUT (FIG. 1B) were recognized.

With regard to the results of the evaluation of the instillation treatment of the dry eye rabbit, the dry eye rabbit model of FIG. 3A was reduced in retention amount of the lacrimal fluid volume as compared to the normal rabbits of FIG. 1A, but high moisture retention was recognized through the instillation of the solution of Example (FIG. 3A). Further, amelioration of the mucin level on the cornea due to dry eye was recognized (FIG. 3B). Besides, early restoration from tear film breakup was also recognized (FIG. 3C and FIG. 3D).

With regard to the results of the evaluation of the instillation treatment of the removed rabbit cornea, when the removed rabbit cornea was subjected to instillation treatment with the solution of Example, the amount of adhering moisture was increased as compared to the solution of Comparative Example (FIG. 2A and FIG. 2B). Further, a prolongation of the time taken for volatilization was recognized (FIG. 2A and FIG. 2B).

On the basis of the above-mentioned results, for the short tear breakup time-type dry eye model to which the solution of Example was instilled, a moisturizing/water-retaining effect on a corneal surface was found after 2 days and 5 days, and thus a therapeutic effect on short tear breakup time-type dry eye was recognized (FIG. 3C). Specifically, it was recognized that short tear breakup time-type dry eye symptoms were fully resolved after 2 days, and this state was maintained even after 5 days. That is, early restoration from tear film breakup was recognized.

Meanwhile, in Comparative Example and Reference Example, therapeutic effects on short tear breakup time-type dry eye were poor even at the time of measurement after 2 days and 5 days, and thus sufficient therapeutic effects on short tear breakup time-type dry eye were not found (FIG. 3C).

INDUSTRIAL APPLICABILITY

The therapeutic agent for short TBUT-type dry eye of the present invention can achieve sufficient moisturization/water retention on a corneal surface, and can induce the production of mucin to express an excellent therapeutic effect on short TBUT-type dry eye.

The invention claimed is:

1. A method of treating short tear breakup time-type dry eye, including the following step:

a step of administering, to a mammal including a human, a copolymer (P) which comprises constituent units represented by the following formulae (1a) to (1c), has a weight-average molecular weight of from 5,000 to 2,000,000, and has a molar ratio among the constituent units [(1a)/(1b)/(1c)] of 100/from 10 to 400/from 2 to 50, or a composition containing the copolymer (P) at a concentration of from 0.001 w/v % to 1.0 w/v %:

(1a)

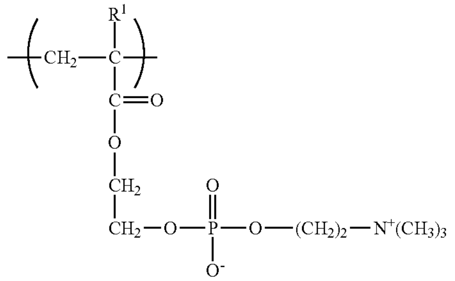

in the formula (1a), $R^1$ represents a hydrogen atom or a methyl group;

(1b)

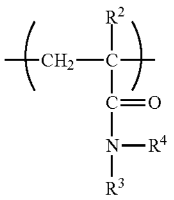

in the formula (1b), $R^2$ represents a hydrogen atom or a methyl group, and $R^3$ and $R^4$ each independently represent a hydrogen atom, a methyl group, or an ethyl group, or represent a morpholino group by being bonded to each other; and

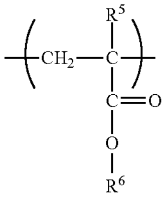

(1c)

in the formula (1c), $R^5$ represents a hydrogen atom or a methyl group, and $R^6$ represents a hydrocarbon group having 12 to 24 carbon atoms.

2. The method of treating short tear breakup time-type dry eye according to claim 1, wherein the copolymer (P) consists of the constituent unit represented by the formula (1a), the constituent unit represented by the formula (1b), and the constituent unit represented by the formula (1c).

3. The method of treating short tear breakup time-type dry eye according to claim 2, wherein the constituent unit represented by the formula (1b) is N,N-dimethylacrylamide, and the constituent unit represented by the formula (1c) is stearyl methacrylate.

4. The method of treating short tear breakup time-type dry eye according to claim 1, wherein the constituent unit represented by the formula (1b) is N,N-dimethylacrylamide, and the constituent unit represented by the formula (1c) is stearyl methacrylate.

* * * * *